US012642855B2

(12) United States Patent
Cooper et al.

(10) Patent No.: US 12,642,855 B2
(45) Date of Patent: Jun. 2, 2026

(54) OLFACTORY DELIVERY SCAFFOLD COMPOUNDS

(71) Applicant: Olfera Corporation, Mountain View, CA (US)

(72) Inventors: Kelvin Cooper, Sarasota, FL (US); Parnian Lak, Mountain View, CA (US); Renaud Renault, Emeryville, CA (US)

(73) Assignee: Olfera Corporation, Mountain View, CA (US)

( * ) Notice: Subject to any disclaimer, the term of this patent is extended or adjusted under 35 U.S.C. 154(b) by 0 days.

(21) Appl. No.: 19/083,391

(22) Filed: Mar. 18, 2025

(65) Prior Publication Data

US 2025/0249106 A1 Aug. 7, 2025

Related U.S. Application Data

(63) Continuation of application No. PCT/US2024/052459, filed on Oct. 22, 2024.

(60) Provisional application No. 63/546,506, filed on Oct. 30, 2023.

(51) Int. Cl.
*A61K 47/54* (2017.01)
*A61K 9/00* (2006.01)

(52) U.S. Cl.
CPC .......... *A61K 47/543* (2017.08); *A61K 9/0043* (2013.01)

(58) Field of Classification Search
USPC .............................................................. 560/1
See application file for complete search history.

(56) References Cited

U.S. PATENT DOCUMENTS

| | | | |
|---|---|---|---|
| 8,299,062 B2 | 10/2012 | Volvovitz | |
| 2014/0364330 A1 | 12/2014 | Mershin et al. | |
| 2019/0055511 A1 | 2/2019 | Villard et al. | |
| 2020/0392490 A1 | 12/2020 | Ziv et al. | |
| 2021/0113558 A1* | 4/2021 | Gendelman ........ | A61K 47/6935 |
| 2022/0340849 A1 | 10/2022 | Pediaditakis et al. | |
| 2025/0269038 A1 | 8/2025 | Cooper et al. | |

FOREIGN PATENT DOCUMENTS

| | | |
|---|---|---|
| WO | 2005102275 A2 | 11/2005 |
| WO | 2018237302 A1 | 12/2018 |
| WO | 2022239001 A1 | 11/2022 |
| WO | 2025076268 A1 | 4/2025 |
| WO | 2025096244 A1 | 5/2025 |

OTHER PUBLICATIONS

Sarukhanyan et al. ACS Omega (2018), 3(5), 5281-5290.*
International Search Report from Appl. No. PCT/US2024/052459, mailed on Jan. 31, 2025.
Kuhns et al., Characterizing novel olfactory receptors expressed in the murine renal cortex, Am J Physiol Renal Physiol, (2019), 317:F172-F186.
Office Action from U.S. Appl. No. 19/083,361, mailed on Sep. 26, 2025.
Ertural et al., RNA Therapeutics: Focus on Antisense Oligonucleotides in the Nervous System, Biomol Ther, (2025), 33:572-581.

* cited by examiner

*Primary Examiner* — Ana Z Muresan
(74) *Attorney, Agent, or Firm* — Nevrivy Patent Law Group P.L.L.C.

(57) ABSTRACT

Exemplary olfactory delivery scaffolds may include 1) an olfactory targeting component, stimulant, or odorant that is recognized by the olfactory nerves via, for example, a smell response, 2) a molecule with biological activity, a therapeutic component, and/or drug (sometimes collectively referred to herein as a “therapeutic component”), and 3) a linker component that links the olfactory targeting component and therapeutic component together. The olfactory delivery scaffolds may be used to deliver a molecule with biological activity and/or a therapeutic component to a subject’s neurological system through the olfactory pathway and pharmaceutical compositions useful in the treatment of neurological and/or neurodegenerative diseases.

10 Claims, 3 Drawing Sheets

101
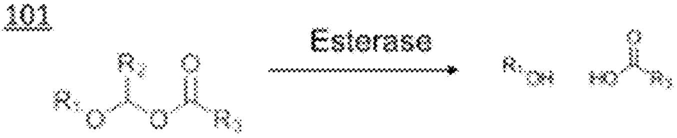
FIG. 1A
| | |
|---|---|
| $R_1OH$ = | 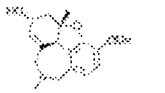 |
| $R_2$ = | H, $C_1$-$C_5$ alkyl |
| $R_3COOH$ = | 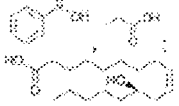 |
102
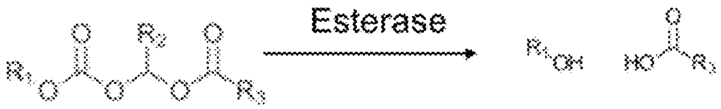
FIG. 1B
| | |
|---|---|
| $R_1OH$ = | 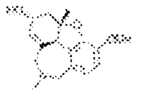 |
| $R_2$ = | H, $C_1$-$C_5$ alkyl |
| $R_3COOH$ = | 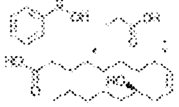 |
103
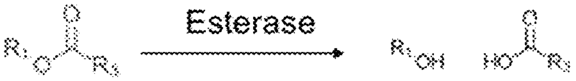
FIG. 1C
| | |
|---|---|
| $R_1OH$ = |  |
| $R_2$ = | H, $C_1$-$C_5$ alkyl |
| $R_3COOH$ = | 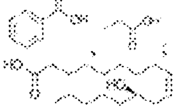 |

201
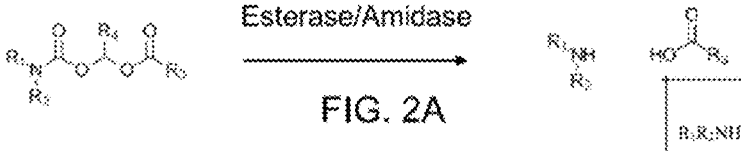
FIG. 2A
| | |
|---|---|
| $R_1R_2NH$ = | 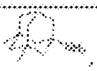, Lecanemab, Aducanumab |
| $R_2$ = | H, $C_1$-$C_6$ alkyl |
| $R_3COOH$ = | 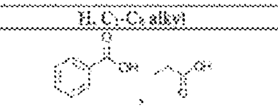 |
| $R_4$ = | H, $C_1$-$C_6$ alkyl |
202
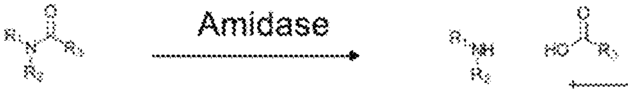
FIG. 2B
| | |
|---|---|
| $R_1R_2NH$ = | 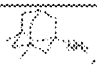, Lecanemab, Aducanumab |
| $R_2$ = | H, $C_1$-$C_6$ alkyl |
| $R_3COOH$ = | 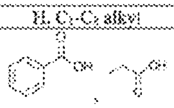 |
| $R_4$ = | H, $C_1$-$C_6$ alkyl |
203
FIG. 2C
| | |
|---|---|
| $R_1R_2NH$ = | 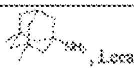, Lecanemab, Aducanumab |
| $R_2$ = | H, $C_1$-$C_6$ alkyl |
| $R_3COOH$ = | 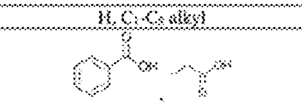 |
| $R_4$ = | H, $C_1$-$C_6$ alkyl |

OLFACTORY DELIVERY SCAFFOLD COMPOUNDS

RELATED APPLICATION

This application is a CONTINUATION of International Application Number PCT/US2024/052459 filed on 22 Dec. 2024, which is a NON-PROVISIONAL of, and claims priority to, U.S. Provisional Patent Application No. 63/546,506 filed on 30 Oct. 2023, and entitled "OLFACTORY DELIVERY SCAFFOLDS AND METHODS FOR USING SAME," which is incorporated in its entirety herein.

TECHNICAL FIELD

The present disclosure relates to olfactory delivery scaffolds, pharmaceutical compositions comprising such olfactory delivery scaffolds and methods of delivering a molecule with biological activity and/or a therapeutic component to a neurological system using such olfactory delivery scaffolds.

BACKGROUND

The olfactory system in mammals is responsible for the sense of smell (olfaction). The olfactory system comprises olfactory epithelium, olfactory bulb, and olfactory cortex and is positioned at the roof of the nasal cavity proximate to the cribriform plate, which is a perforated portion of the ethmoid bone separating the frontal lobe of the cerebrum from the nasal cavity. Because the olfactory system is not isolated from the brain by the blood-brain barrier, it provides a pathway to deliver molecules and particles (e.g., pesticides, metals, pathogens, etc.) via inhalation into the nasal cavity and to the brain. This pathway is established by olfactory epithelium that use intracellular, paracellular, and/or transcellular transport of molecules and/or particles via, for example, endocytosis into olfactory sensory neurons. This intracellular, paracellular, and/or transcellular transport is followed by intraneuronal transport of the molecules or particles along axons of olfactory sensory neurons, through the cribriform plate, into the olfactory bulb, and finally into the brain. This pathway avoids absorption into a subject's systemic circulation and the subsequent transport across and/or through their blood/brain barrier.

SUMMARY

The present disclosure provides olfactory delivery scaffolds capable of delivering therapeutic components to a subject's neurological system (e.g., brain) through the olfactory pathway and treating neurological and/or neurodegenerative diseases such as, but not limited to, Parkinson's disease, Alzheimer's disease, amyotrophic lateral sclerosis (ALS), multiple sclerosis (MS), Huntington's disease, and/or multiple system atrophy. The present disclosure also provides pharmaceutical compositions and methods for delivering a molecule with biological activity and/or a therapeutic component to a subject's neurological system through the olfactory pathway for the treatment of neurological and/or neurodegenerative diseases.

According to embodiments of the present disclosure, the olfactory delivery scaffolds disclosed herein may include three components: 1) an olfactory targeting component, stimulant, or odorant that is recognized by the olfactory nerves via, for example, a smell response, 2) a therapeutic component, a molecule with biological activity, and/or a drug (sometimes collectively referred to herein as a "therapeutic component"), and 3) a linker component that links the olfactory targeting component and therapeutic component together. When the olfactory delivery scaffold is introduced into the nasal cavity, it is cleaved by enzymes (e.g., esterase, amidase, nuclease, and/or hydrolase) present in the nasal mucus into an olfactory targeting component and a separate therapeutic component that traverses the cribriform plate to travel into the olfactory bulb and eventually into the brain or central nervous system without having the cross the blood-brain barrier. In addition, the scaffold can enter the olfactory system via intracellular, paracellular, and/or transcellular transport of molecules and/or particles via, for example, endocytosis into olfactory sensory neurons and then be cleaved by enzymes to deliver the therapeutic component.

BRIEF DESCRIPTION OF THE FIGURES

The present disclosure is illustrated by way of example, and not limitation, in the figures of the accompanying drawings in which:

FIG. 1A is a diagram of a reaction that exposes a first single-component olfactory delivery scaffold and/or cleaves the first single-component olfactory delivery scaffold into two separate components, in accordance with one or more embodiments of the present disclosure;

FIG. 1B is a diagram of a reaction that exposes a second single-component olfactory delivery scaffold and/or cleaves the second single-component olfactory delivery scaffold into two separate components, in accordance with one or more embodiments of the present disclosure;

FIG. 1C is a diagram of a reaction that exposes a third single-component olfactory delivery scaffold and/or cleaves the third single-component olfactory delivery scaffold into two separate components, in accordance with one or more embodiments of the present disclosure;

FIG. 2A is a diagram of a reaction that exposes a fourth single-component olfactory delivery scaffold to esterase and/or amidase, which cleaves the fourth single-component olfactory delivery scaffold into two separate components, in accordance with one or more embodiments of the present disclosure;

FIG. 2B is a diagram of a reaction that exposes a fifth single-component olfactory delivery scaffold to amidase, which cleaves the fifth single-component olfactory delivery scaffold into two separate components, in accordance with one or more embodiments of the present disclosure;

FIG. 2C is a diagram of a reaction that exposes a sixth single-component olfactory delivery scaffold to esterase, which cleaves the sixth single-component olfactory delivery scaffold into two separate components, in accordance with one or more embodiments of the present disclosure;

Figure 3A:
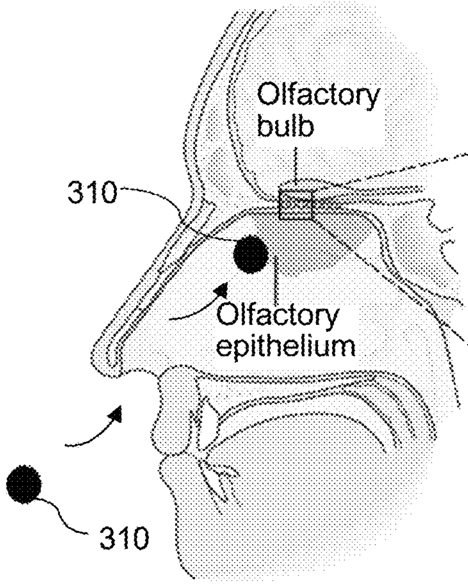
FIG. 3A is a cross-section of a portion of a subject's head with a delivery route for one or more olfactory delivery scaffolds to the subject's central nervous system, in accordance with one or more embodiments of the present disclosure.

Throughout the drawings, the same reference numerals, and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

DETAILED DESCRIPTION

Unless otherwise noted, the term "for example" or "e.g.," as used herein, is used merely by way of example, and should not be construed as limiting the present disclosure to only those items explicitly referred to in the specification.

Unless otherwise noted, the terms "pharmaceutical composition" and "dosage form" may be interchangeably used herein and are defined to mean a composition, preparation, or system in which doses of olfactory delivery scaffold are included.

Unless otherwise noted, the terms "subject" and "patient" may be interchangeably used herein and may mean all members of the animal kingdom and/or mammals (e.g. humans).

Unless otherwise noted, the term "alkyl", by itself or as part of another substituent means, unless otherwise stated, may be a straight, branched, or cyclic chain hydrocarbon having the number of carbon atoms designated (i.e. $C_1$-$C_8$ means one to eight carbons) and may include straight, branched chain, and/or cyclic groups, such as, but not limited to, methyl, ethyl, propyl, isopropyl, butyl, isobutyl, tert-butyl, pentyl, neopentyl, hexyl, cyclopentyl, cyclohexyl, and cyclopropylmethyl.

The cells within the olfactory pathway and, in particular, olfactory epithelium, are known to have rapid regeneration cycles and the olfactory delivery scaffolds disclosed herein may leverage these regenerative mechanisms to, for example, increase efficacy of drug delivery and/or performance.

The olfactory delivery scaffolds disclosed herein may include three components: 1) an olfactory targeting component, stimulant, or odorant that is recognized by the olfactory nerves via, for example, a smell response, 2) a molecule with biological activity and/or a therapeutic component or drug, and 3) a linker component that links the olfactory targeting component and therapeutic component together. In some embodiments, the olfactory delivery scaffold may also include one or more delivery components such as an excipient (e.g., water for injection (WFI)) that may be used to aid in delivery of the olfactory delivery scaffold to a patient's olfactory system. Additionally, or alternatively, the delivery component may be selected to target the olfactory system (e.g., an odorant) and ease communication of the therapeutic component through the olfactory system and into the brain. Also, the prodrug approach will be used to enhance the half-life of the active ingredient and increase its chance of passing the mucosal layer to get exposed to the olfactory epithelium. For example, the delivery component may have physicochemical properties selected and/or designed to facilitate the delivery of the therapeutic component to the olfactory system and/or olfactory epithelium, which may act to enhance delivery of the therapeutic component to the brain and/or central nervous system via, for example, intracellular transport.

The linker component of the olfactory delivery scaffold may have one or more characteristics that enable cleavage of the olfactory delivery scaffold within the olfactory system via enzymes that may be commonly found in the olfactory system (e.g., mucus within the nasal cavity and/or intracellular enzymes) such as esterase, amidase, nuclease, and hydrolase, cathepsin as well as pH sensitive linkers. In some embodiments, the linker component may be a covalent linker such as acetals, ketals, aminals, esters, amides, and phosphates.

The olfactory targeting compound may be, for example, an odorant known to be safe for humans. Often times, the olfactory targeting compound may have a strong smell and/or a low vapor pressure so that, for example, a relatively small quantity of the olfactory targeting compound may stimulate the olfactory nerves and/or trigger a smell response. Exemplary olfactory targeting compounds include, but are not limited to, benzoic acid, lysine, glutamic acid, and castor oil. In addition to triggering a smell response, in some embodiments, the olfactory targeting compound may also stimulate regeneration of olfactory nerves (e.g., olfactory epithelium).

The therapeutic component may be any chemical, small or large molecule, therapeutic agent, and/or pharmaceutical that may have an impact on a patient's brain, neurological system, and/or central nervous system. In some cases, the therapeutic component may be a treatment for one or more neurodegenerative diseases such as Parkinson's Disease and/or Alzheimer's Disease. Exemplary therapeutic components include, but are not limited to, anti-neurodegeneration compounds, neurologically therapeutic compounds, antibodies, therapeutic proteins, gene therapy components, acetylcholine esterase inhibitors (e.g., donepezil, rivastigmine, and/or galantamine), NMDA antagonist compounds (e.g., memantine), and a combination of memantine and donepezil, dopamine, L-Dopa, and/or compounds that target the amyloid-β protein, thought to be a key factor in the loss of neurological function through the formation of amyloid-β plaque.

The olfactory delivery scaffolds disclosed herein may include, for example, a single compound chemically derived from one or more olfactory targeting components, one or more therapeutic components, and a linker component that links the olfactory targeting component and therapeutic component together via, for example, enzymatic action. Additionally, or alternatively, the olfactory delivery scaffold disclosed herein may be formulation (e.g., mixture, suspension, solution, etc.) comprising one or more olfactory targeting components, one or more therapeutic components, linked by the formulation.

Two exemplary schemes for the use of an olfactory delivery scaffold in the form of a single-component (e.g., single synthesized molecule) olfactory delivery scaffold are provided by FIGS. 1A-1C and FIGS. 2A-2C, respectively. The six exemplary single-component olfactory delivery scaffolds of FIGS. 1A-1C and FIGS. 2A-2C show the single-component olfactory delivery scaffolds before (on the left side of the page) and after (on the right side of the page) they undergo cleavage by an enzyme (e.g., esterase and/or amidase) that effectively unlinks the single-component olfactory delivery scaffold into a separate therapeutic component and an olfactory targeting component and, in some cases, the linker fragments.

The first scheme reactions shown in FIGS. 1A-1C have a key that provides information about the various components of the reactions, wherein $R_1$ is a molecule with biological activity and/or a therapeutic component and/or anti-neurodegeneration molecule; $R_3$ is an olfactory stimulation compound, or odorant; and $R_2$ is a linker that links $R_1$ (i.e., the therapeutic component) and $R_3$ (i.e., the olfactory stimulation compound) such as benzoic acid, ethonic acid, carbolic acid, propanoic acid, and/or castor oil. $R_2$ may be, for example, hydrogen and/or $C_1$-$C_8$ alkyl. The enzyme esterase is the unlinking enzyme present in the reactions of FIGS. 1A-1C. Esterase is an enzyme commonly found in nasal mucus and, when the olfactory delivery scaffold is introduced into the nasal cavity it is cleaved by esterase into a molecule with biological activity and/or a therapeutic component (e.g., an alcohol) and an olfactory stimulant component (e.g., an odorant and/or acid).

In particular, the reaction of FIG. 1A exposes a first single-component olfactory delivery scaffold 101:

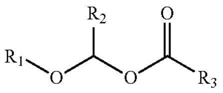

to esterase, which cleaves first single-component olfactory delivery scaffold 101 into the therapeutic component $R_1$—OH, which may be an alcohol, and an olfactory targeting component HOOC—$R_3$, which may be an acid. In some embodiments, the reaction of FIG. 1A (i.e., the first scheme) may release the linker portion as one fragment.

The reaction of FIG. 1B exposes a second single-component olfactory delivery scaffold 102:

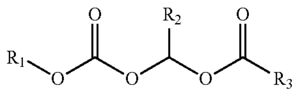

to esterase, which cleaves second single-component olfactory delivery scaffold 102 into the therapeutic component $R_1$—OH, which may be an alcohol, and an olfactory targeting component HOOC—$R_3$, which may be an acid. In some embodiments, the reaction of FIG. 1B (i.e., the second scheme) may release the linker portion as two fragments.

The reaction of FIG. 1C exposes a third single-component olfactory delivery scaffold 103:

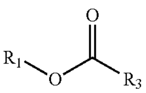

to esterase, which cleaves third single-component olfactory delivery scaffold 103 into the therapeutic component $R_1$—OH, which may be an alcohol, and an olfactory targeting component HOOC—$R_3$, which may be an acid.

The reactions shown in FIGS. 2A-2C have a key that provides information about the various components of the reactions, wherein $R_1R_2NH$ is a molecule with biological activity and/or a therapeutic component such as Lecanemab, Aducanumab, and/or:

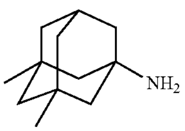

$R_3$ is an olfactory targeting component, or odorant; and $R_4$ is a linker that links the therapeutic component ($R_1R_2NH$) and the olfactory stimulation compound ($R_3$). $R_4$ may be, for example, hydrogen and/or $C_1$-$C_8$ alkyl.

The reaction of FIG. 2A exposes a fourth single-component olfactory delivery scaffold 201 to esterase and/or amidase (an enzyme commonly found in nasal mucus), which cleaves fourth single-component olfactory delivery scaffold 201:

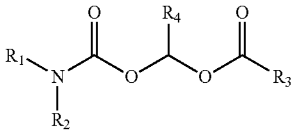

into the therapeutic component:

and the olfactory targeting component, HOOC—$R_3$, which may be an acid. In some embodiments, the reaction of FIG. 2A may release the linker portion as two fragments.

The reaction of FIG. 2B exposes a fifth single-component olfactory delivery scaffold 202:

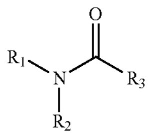

to amidase, which cleaves fifth single-component olfactory delivery scaffold 202 into the therapeutic component:

and the olfactory targeting component, HOOC—$R_3$, which may be an acid.

The reaction of FIG. 2C exposes a sixth single-component olfactory delivery scaffold 203:

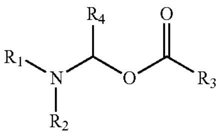

to esterase, which cleaves sixth single-component olfactory delivery scaffold 203 into the therapeutic component

and the olfactory targeting component, HOOC—$R_3$, which may be an acid. In some embodiments, the reaction of FIG. 2C may release the linker portion as one fragment.

In one embodiment, the present disclosure is directed to a compound of formula A:

FORMULA A

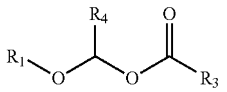

wherein, $R_1OH$ is a therapeutic component and/or molecule with biological activity whose target is a brain localized receptor, enzyme, ion channel, and/or RNA; $R_2$ is H or $C_1$-$C_8$alkyl; and $R_3$ $CO_2H$ is a molecule that interacts with one or more olfactory receptor(s). In some embodiments, the compound of formula A is and/or may include a compound of formula I:

| | |
|---|---|
| Compound of formula I | [(1S,3R,15R)-12-Methoxy-1-methyl-7-methyl-16-oxa-7-azatetracyclo[11.2.1.$0^{5,15}$.$0^{9,14}$]hexadeca-4,9,11,13-tetraen-3-yloxy]methyl (9Z,12R)-12-hydroxy-9-octadecenoate. 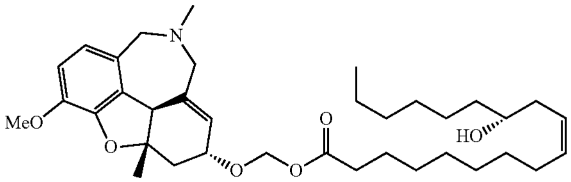 [SMILES: CCCCCC[C@@H](O)C/C=C\CCCCCCCC(=O)OCO[C@H]1C=C2CN(C)Cc3ccc(OC)c4c3[C@@H]2[C@](C)(C1)O4] |

In another embodiment, the present disclosure is directed to a compound of formula B, as shown below:

FORMULA B

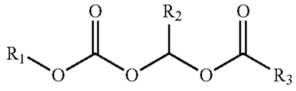

wherein, $R_1OH$ is a molecule with biological activity and/or a therapeutic component whose target is a brain localized receptor, enzyme, ion channel, and/or RNA; $R_2$ is H or $C_1$-$C_8$alkyl; and $R_3$ $CO_2H$ is a molecule that interacts with one or more olfactory receptor(s). In certain embodiments, the compound of formula B is a compound of formula J, as shown below:

| | |
|---|---|
| Compound of formula J | {[(1S,3R,15R)-12-Methoxy-1-methyl-7-methyl-16-oxa-7-azatetracyclo[11.2.1.$0^{5,15}$.$0^{9,14}$]hexadeca-4,9,11,13-tetraen-3-yl](oxycarbonyloxy)}methyl (9Z,12R)-12-hydroxy-9-octadecenoate. 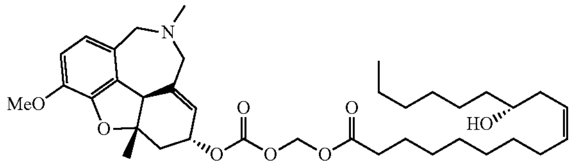 [SMILES: CCCCCC[C@@H](O)C/C=C\CCCCCCCC(=O)OCOC(=O)O[C@H]1C=C2CN(C)Cc3ccc(OC)c4c3[C@@H]2[C@](C)(C1)O4] |

In another embodiment, the present disclosure is directed to a compound of formula C, as shown below:

FORMULA C

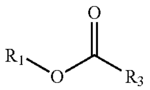

wherein, $R_1OH$ is a molecule with biological activity and/or a therapeutic component whose target is a brain localized receptor, enzyme, ion channel, and/or RNA; and $R_3CO_2H$ is a molecule that interacts with an olfactory receptor. At times, the compound of formula C is a compound of formula K, as shown below:

| | |
|---|---|
| Compound of formula K | (1S,3R,15R)-12-Methoxy-1-methyl-7-methyl-16-oxa-7-azatetracyclo[11.2.1.$0^{5,15}$.$0^{9,14}$]hexadeca-4,9,11,13-tetraen-3-yl (9Z,12R)-12-hydroxy-9-octadecenoate. 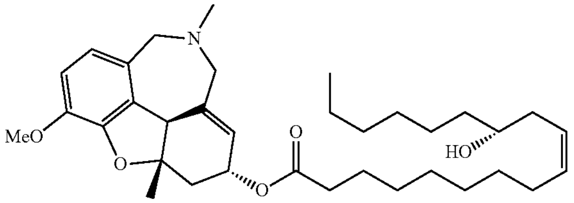 [SMILES: CCCCCC[C@@H](O)C/C=C\CCCCCCCC(=O)O[C@H]1C=C2CN(C)Cc3ccc(OC)c4c3[C@@H]2[C@](C)(C1)O4] |

In another embodiment, the present disclosure is directed to a compound of formula D, as shown below:

FORMULA D

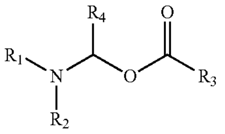

wherein, $R_1R_2NH$ is a molecule with biological activity and/or a therapeutic component whose target is a brain localized receptor, enzyme, ion channel, and/or RNA; $R_4$ is H or $C_1$-$C_8$alkyl; and $R_3CO_2H$ is a molecule that interacts with one or more olfactory receptor(s). In certain embodiments, the compound of formula D is a compound of a formula L, as shown below:

Compound of formula L — [(1r,3R,5S,7S)-3,5-Dimethyl-1-adamantanylamino]methyl (9Z,12R)-12-hydroxy-9-octadecenoate.

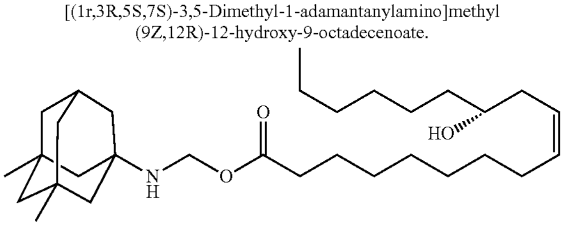

In another embodiment, the present disclosure is directed to a compound of formula E, as shown below:

FORMULA E

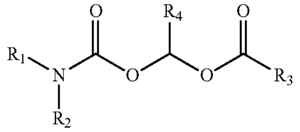

wherein, $R_1R_2NH$ is a molecule with biological activity and/or a therapeutic component whose target is a brain localized receptor, enzyme, ion channel, and/or RNA; $R_4$ is H or $C_1$-$C_8$alkyl; and $R_3CO_2H$ is a molecule that interacts with one or more olfactory receptor(s).

In certain embodiments, the compound of formula E may have a structure of a compound of formula M, a compound of formula Q, a compound of formula R, a compound of formula T, a compound of formula U, a compound of formula V, and/or a compound of formula X, each of which are shown and detailed below:

Compound of formula M — {[(1r,3R,5S,7S)-3,5-Dimethyl-1-adamantanyl](aminocarbonyloxy)}methyl (9Z,12R)-12-hydroxy-9-octadecenoate.

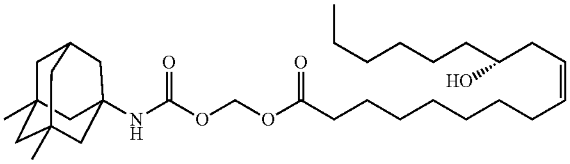 [SMILES: CCCCCC[C@@H](O)C/C=C\CCCCCCCC(=O)OCOC(=O)NC12CC3CC(C)(CC(C)(C3)C1)C2]

Compound of formula Q — (R)-4-Amino-4-(1-{[2-(3,4-dihydroxyphenyl)ethyl](aminocarbonyloxy)}ethoxycarbonyl) butyric acid.

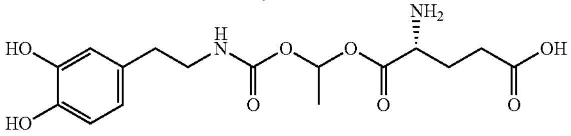

Compound of formula R — (R)-2-Amino-4-(1-{[2-(3,4-dihydroxyphenyl)ethyl](aminocarbonyloxy)}ethoxycarbonyl) butyric acid.

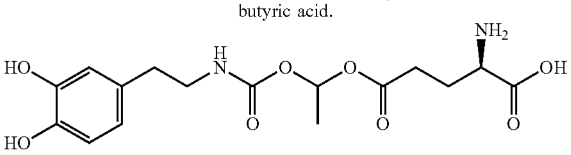

Compound of formula T — 1-{[2-(3,4-Dihydroxyphenyl)ethyl](aminocarbonyloxy)}ethyl (R)-2,6-diaminohexanoate.

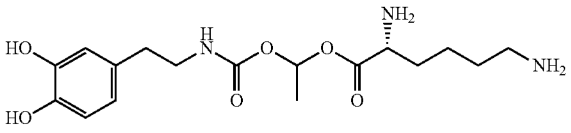 [SMILES: CC(OC(=O)NCCc1ccc(O)c(O)c1)OC(=O)[C@H](N)CCCCN]

Compound of formula U — 2-(3,4-Dihydroxyphenyl)ethyl 1-[(2R,3R,4R,5S)-2,3,4,5-tetrahydroxy-6-(methylamino)hexyloxy]-1-ethanecarbamate.

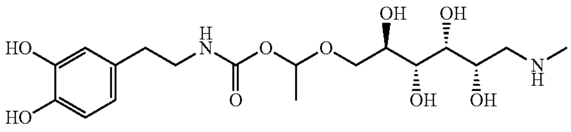 [SMILES: CNC[C@H](O)[C@@H](O)[C@H](O)[C@H](O)COC(C)OC(=O)NCCc1ccc(O)c(O)c1]

-continued

Compound of formula V

2-{4-[2-(1-{[2-(3,4-Dihydroxyphenyl)ethyl](aminocarbonyloxy)}ethoxy)ethyl]-1-piperazinyl}ethanesulfonic acid.

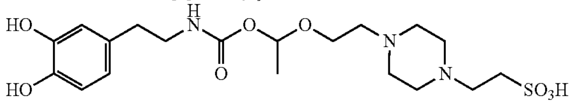

Compound of formula X

1-{[2-(3,4-Dihydroxyphenyl)ethyl](aminocarbonyloxy)}ethyl (9Z,12R)-12-hydroxy-9-octadecenoate.

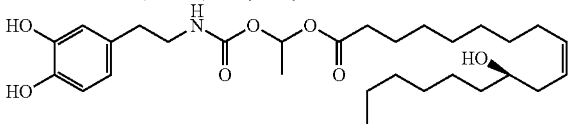

In another embodiment, the present disclosure is directed to a compound of formula F, as shown below:

FORMULA F

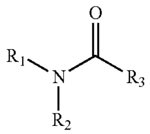

wherein, $R_1R_2NH$ is a molecule with biological activity and/or a therapeutic component whose target is a brain localized receptor, enzyme, ion channel, and/or RNA; and $R_3CO_2H$ is a molecule that interacts with one or more olfactory receptor(s). In certain embodiments, the compound of formula F may have a structure of a compound of formula N, a compound of formula O, a compound of formula P, a compound of formula S, and/or a compound of formula W, each of which are described and shown below:

Compound of formula N

N-[(1r,3R,5S,7S)-3,5-Dimethyl-1-adamantanyl]-(9Z,12R)-12-hydroxy-9-octadecenamide.

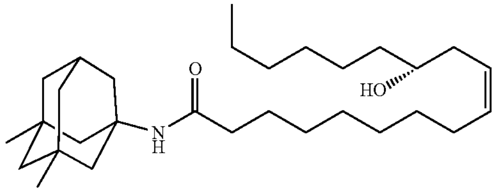 [SMILES: CCCCCC[C@@H](O)C/C=C\CCCCCCCC(=O)NC12CC3CC(C)(CC(C)(C3)C1)C2]

Compound of formula O (R)-2-Amino-4-[N-2-(3,4-dihydroxyphenyl)ethylcarbamoyl]butyric acid.

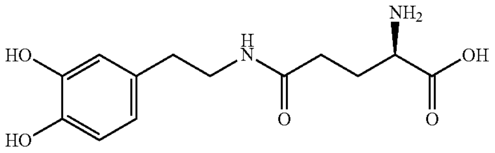 [SMILES: N[C@H](CCC(=O)NCCc1ccc(O)c(O)c1)C(=O)O]

Compound of formula P (R)-4-Amino-4-[N-2-(3,4-dihydroxyphenyl)ethylcarbamoyl]butyric acid.

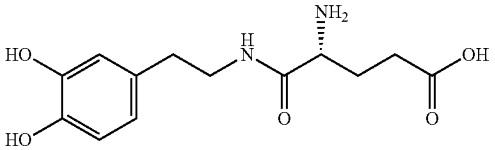 [SMILES: N[C@H](CCC(=O)O)C(=O)NCCc1ccc(O)c(O)c1]

Compound of formula S

N-[2-(3,4-Dihydroxyphenyl)ethyl](R)-2,6-diaminohexanamide.

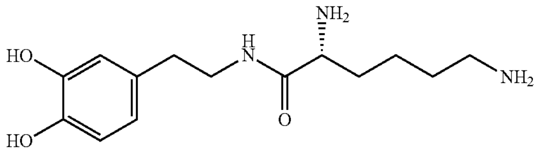 [SMILES: NCCCC[C@@H](N)C(=O)NCCc1ccc(O)c(O)c1]

-continued

Compound of formula W

N-[2-(3,4-Dihydroxyphenyl)ethyl]-(9Z,12R)-12-hydroxy-9-octadecenamide.

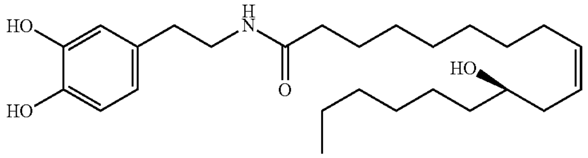 [SMILES: CCCCCC[C@@H](O)C/C=C\CCCCCCCC(=O)NCCc1ccc(O)c(O)c1]

In another embodiment, the present disclosure is directed to a compound of formula G, as shown below:

FORMULA G

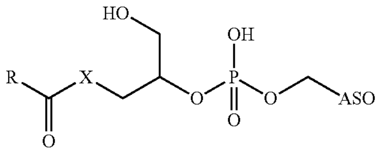

wherein, $RCO_2H$ is a molecule that interacts with one or more olfactory receptor(s); X is O or NH; and ASO represents an antisense oligonucleotide attached at the 3' or 5' position, wherein the ASO has biological activity, whose target is a brain localized RNA.

In another embodiment, the present disclosure is directed to a compound of formula H, as shown below:

FORMULA H

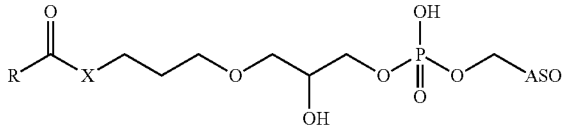

wherein, $RCO_2H$ is a molecule that interacts with one or more olfactory receptor(s); X is O or NH; and ASO represents an antisense oligonucleotide attached at the 3' or 5' position, wherein the ASO has biological activity whose target is a brain localized RNA. In some embodiments, the compound of formula H has a structure of a compound of formula Y and/or a compound of formula Z, as shown and described below:

Compound of formula Y

N-{3-[2-Hydroxy-3-(hydroxy-3'- or 5'-ASO-oxyphosphoryloxy)propoxy]propyl}(S)-2,6-diaminohexanamide.

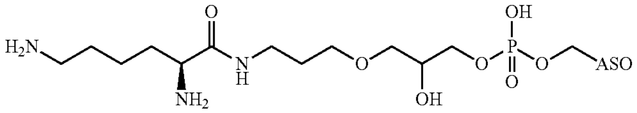

Compound of formula Z

N-{3-[2-Hydroxy-3-(hydroxy-3'- or 5'-ASO-oxyphosphoryloxy)propoxy]propyl}-(9Z,12R)-12-hydroxy-9-octadecenamide.

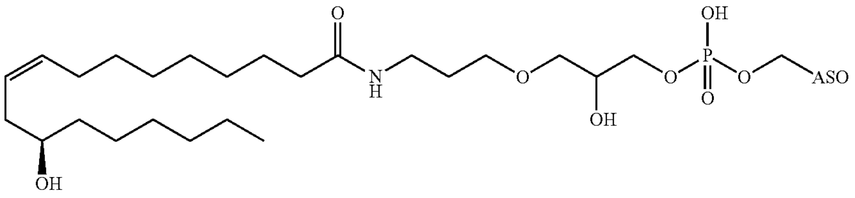

When employed as pharmaceuticals, the compounds, formulas, and/or olfactory delivery scaffolds provided herein can be administered in the form of pharmaceutical compositions, especially when formulated for intranasal administration to humans, the compounds and/or olfactory delivery scaffolds disclosed herein may be preferably combined with at least one pharmaceutically acceptable carrier or excipient. Such carriers or excipients may be known to those of skill in the art and may include, without limitation, acidifying agents, emulsifiers, pH regulators, chelating agents, preservatives, thickening agents, co-solvents, permeation enhancers, mucoadhesives, absorption enhancing agents and/or absorption enhancing vehicles. Examples of such and other carriers or excipients can be found in "Handbook of Pharmaceutical Excipients"; Ed. A. H. Kibbe, 3rd Ed., American Pharmaceutical Association, USA and Pharmaceutical Press UK, 2000. The pharmaceutical compositions can include a therapeutically effective amount of the compounds and/or olfactory delivery scaffolds disclosed herein, which make up from 0.01% to 90% by weight of the composition. The pharmaceutical compositions may be prepared by any of the methods well known in the art of pharmacy. Information about formulation techniques can be found in, for example, Remington's Pharmaceutical Sciences (Mack Publishing Co., Easton, PA). In general, the pharmaceutical compositions are prepared by uniformly and intimately bringing into association one or more compounds and/or olfactory delivery scaffolds disclosed herein with a liquid carrier (e.g., water for injection) which may constitute one or more accessory ingredients.

In some embodiments, the present disclosure is directed to a pharmaceutical composition for intranasal administration, comprising a compound of a formula provided herein and a pharmaceutically acceptable carrier.

The present disclosure further provides a pharmaceutical composition and/or scaffold for administering a molecule with biological activity and/or a therapeutic component to the nasal cavity of a subject and delivering the molecule and/or therapeutic component through the olfactory pathway to a neurological system of the subject, comprising a compound provided herein and a pharmaceutically acceptable carrier. In certain embodiments, the neurological system is brain or central nervous system. In some embodiments, the therapeutic component is a therapeutic agent and/or a pharmaceutical that has an impact on, for example, a subject's brain, neurological system, and/or central nervous system.

The present disclosure further provides a method for administering a molecule with biological activity and/or a therapeutic component to a neurological system of a subject, comprising: administering a pharmaceutical composition comprising a compound provided herein and a pharmaceutically acceptable carrier to the nasal cavity of the subject, wherein the compound undergoes cleavage by an enzyme that unlinks the compound into a molecule with biological activity and/or a therapeutic component and an olfactory targeting component, and wherein the molecule with biological activity and/or therapeutic component may be absorbed through the nasal cavity and olfactory system of a subject and transported to the neurological system (e.g., brain and/or central nervous system) of the subject. In some embodiments, the molecule therapeutic component is a therapeutic agent and/or a pharmaceutical that has an impact on a subject's brain, neurological system, and/or central nervous system.

The present disclosure further provides a method of treating a neurological and/or a neurodegenerative disease in a subject, comprising administering a pharmaceutical composition comprising a compound provided herein and a pharmaceutically acceptable carrier to the nasal cavity of the subject. In certain embodiments, the neurological and/or neurodegenerative disease can be selected from Parkinson's disease, Alzheimer's disease, amyotrophic lateral sclerosis (ALS), multiple sclerosis (MS), Huntington's disease, multiple system atrophy, and a combination thereof.

In some embodiments, the present disclosure is directed to a formulated olfactory delivery scaffold which may include, for example, a formulation of 1) at least one olfactory targeting component, stimulant, or odorant that is recognized by the olfactory nerves via, for example, a smell response), 2) at least one therapeutic component, molecule that is biologically active, and/or drug, and 3) a delivery component in the form of, for example, an excipient such as water for injection (WFI). In first example, a formulated olfactory delivery scaffold may be buffered to a pH of 6.5-7.5 and may comprise:

80-95% WFI,
2-8% castor oil,
0.5-1% emulsifier,
1-2% preservative, and
a molecule with biological activity and/or a therapeutic component such as L-Dopa, dopamine, donepezil, rivastigmine, galantamine, and/or memantine at therapeutic dose level.

In a second example, a formulated olfactory delivery scaffold may be buffered to a pH of 6.5-7.5 and may comprise:

80-95% WFI,
2-8% castor oil,
0.5-1% emulsifier,
1-2% preservative, and
a molecule with biological activity and/or a therapeutic component such as Lecanemab and/or Aducanumab at therapeutic dose level.

In a third example, a formulated olfactory delivery scaffold may be buffered to a pH of 6.5-7.5 and may comprise:

80-95% WFI,
benzoic acid,
1-2% preservative, and
a molecule with biological activity and/or a therapeutic component such as donepezil, rivastigmine, galantamine, and/or memantine at therapeutic dose level.

In a fourth example, a formulated olfactory delivery scaffold may be buffered to a pH of 6.5-7.5 and may comprise:

80-95% WFI,
benzoic acid,
1-2% preservative, and
a molecule with biological activity and/or a therapeutic component such as Lecanemab and/or Aducanumab at therapeutic dose level.

In a particular embodiment, the present disclosure provides a pharmaceutical composition for administering a molecule with biological activity, drug, and/or a therapeutic component to the nasal cavity of a subject so that it may be delivered to a neurological system of a subject through the subject's olfactory pathway. In this embodiment, the pharmaceutical composition may comprise, by weight of the composition:

80-95% of water for injection (WFI);
2-8% of castor oil;
0.5-1% of an emulsifier;
1-2% of a preservative; and a molecule with biological activity and/or a therapeutic component at a therapeutic dose level, wherein the composition has a pH of 6.5-7.5.

In another embodiment, the present disclosure provides a pharmaceutical composition for administering a molecule with biological activity and/or a therapeutic component to the nasal cavity of a subject so that it may be delivered to a neurological system of a subject through the subject's olfactory pathway and, in this embodiment, the pharmaceutical composition comprises, by weight of the composition:

80-95% of water for injection (WFI);

2-8% of benzoic acid;

1-2% of a preservative; and a molecule with biological activity and/or a therapeutic component at a therapeutic dose level, wherein the composition has a pH of 6.5-7.5.

Exemplary therapeutic components, drugs, and/or molecules with biological activity disclosed herein may be, but are not limited to, L-Dopa, dopamine, donepezil, rivastigmine, galantamine, memantine, lecanemab, aducanumab, and combinations thereof.

Figure 3B:
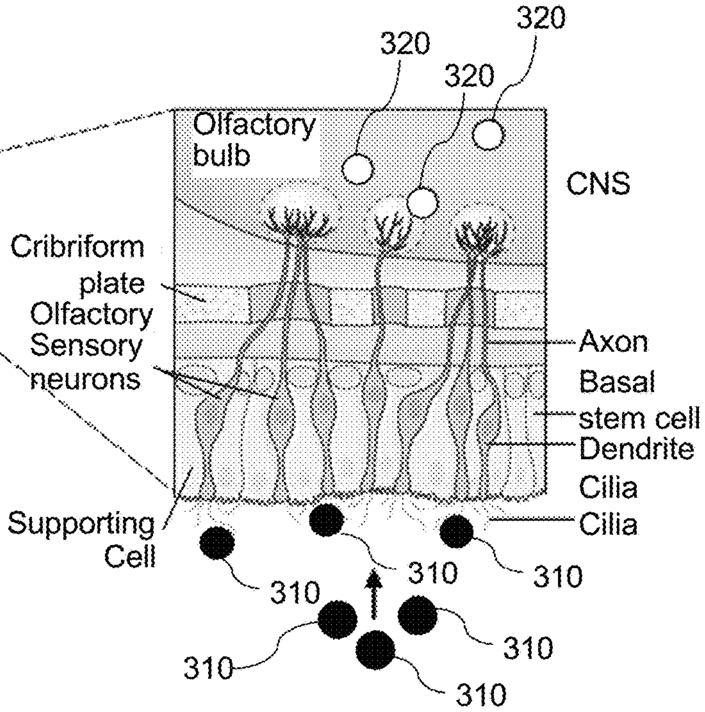
FIG. 3B is a close-up view of a portion of the subject's head shown in FIG. 3A, in accordance with one or more embodiments of the present disclosure.

In some embodiments, the olfactory delivery scaffolds (or compounds) disclosed herein may be used to, for example, deliver therapeutic components, molecule with biological activity, and/or drugs to a subject's neurological system (e.g., brain) and/or treat a neurological and/or neurodegenerative condition such as Parkinson's disease, Alzheimer's disease, amyotrophic lateral sclerosis (ALS), multiple sclerosis (MS), Huntington's disease, and/or multiple system atrophy. For example, an olfactory delivery scaffold may be placed (e.g., sprayed, injected, and/or inhaled) within an olfactory system of the subject for communication to the subject's central nervous system via, for example, transmission of the olfactory delivery scaffold through, for example, intracellular transport of the olfactory delivery scaffold via, for example, endocytosis into olfactory sensory neurons followed by intraneuronal transport along axons and through the cribriform plate into the olfactory bulb and on to the central nervous system as shown in, for example, FIGS. 3A-3C to treat the neurological and/or neurodegenerative condition, wherein FIG. 3A provides an illustration of a cross-section of a portion of a subject's head with a delivery route (shown in arrows with solid lines) for olfactory delivery scaffold particles 310 (shown as black circles) to the subject's central nervous system via the olfactory epithelium and olfactory bulb. Olfactory delivery scaffold particles 310 may be, for example, dry particles and/or droplets of material including single-component olfactory delivery scaffold molecules, examples of which are provided herein and above with regard to FIGS. 1A-1C and 2A-2C and/or a formulated olfactory delivery scaffold as, for example, disclosed herein. As olfactory delivery scaffold particles 310 travel through the nasal cavity to the cilia, or olfactory epithelium, they may be cleaved by enzymes (e.g., esterase, amidase, nuclease, and/or hydrolase)) present in the nasal mucus or intracellular space into olfactory targeting components (not shown) and separate molecules with biologic activity, drugs, and/or therapeutic components 320 (collectively referred to herein as "therapeutic components 320") that traverse the cribriform plate to travel into the olfactory bulb and eventually into the brain, or central nervous system, as shown in FIG. 3B, which is a close-up view of a portion of the subject's head shown in FIG. 3A and shows how olfactory delivery scaffold particles 310 are transported from the cilia through the olfactory sensory neurons, cribriform plate, and into the olfactory bulb for communication to the subject's olfactory bulb and central nervous system (CNS) or brain. The olfactory targeting components may dock with the subject's olfactory receptors or other receptors in the olfactory epithelium and/or move into the brain as, for example, shown in FIG. 3B.

Figure 3C:
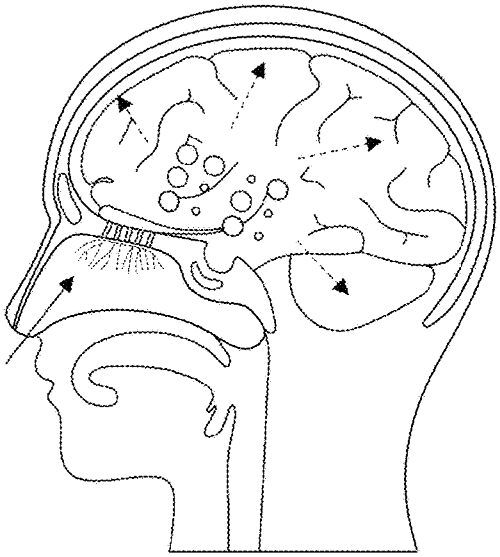
FIG. 3C is a cross-section of a subject's head showing a delivery route for one or more olfactory delivery scaffolds to the subject's brain and how the one or more olfactory delivery scaffolds may travel through the subject's brain, in accordance with one or more embodiments of the present disclosure.

FIG. 3C is a cross-section of an alternative subject's head showing a delivery route (shown as a solid black arrow) for olfactory delivery scaffold particles 310 to travel through the nasal cavity and up into the subject's brain. FIG. 3C also shows (via dashed arrows) how therapeutic components 320 may travel through the subject's brain to, for example, treat a neurological condition.

EXAMPLES

The present disclosure is further explained in the form of following examples and exemplary methods (e.g., processes for manufacturing the compositions and/or compounds using, for example, one or more formulas described herein). However, it is to be understood that the examples are merely illustrative and are not to be taken as limitations upon the scope of the invention. Various changes and modifications to the disclosed embodiments and examples will be apparent to those skilled in the art and such changes and modifications may be made without departing from the scope of the invention.

In a first example, a compound 1 may be prepared from Cbz-glutamic acid α-benzyl ester 11 via a DCI mediated coupling with dibenzyl dopamine 12, followed by deprotection by hydrogenation in the presence of Pd/C as shown in, for example, Scheme 1, below.

SCHEME 1

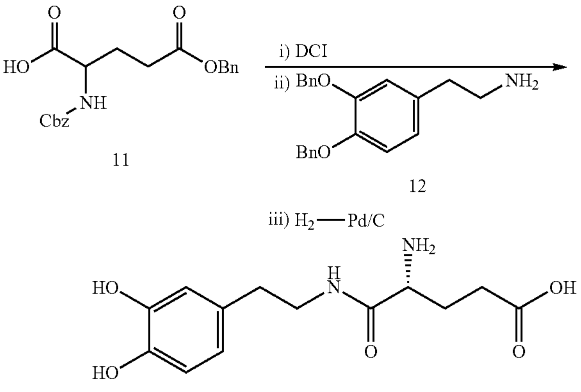

11

12

1

In second example, a compound 2 may be prepared from Cbz-glutamic acid benzyl ester 13 via a DCI mediated coupling with dibenzyl dopamine 12, followed by deprotection by hydrogenation in the presence of Pd/C as shown in, for example, Scheme 2, below.

SCHEME 2

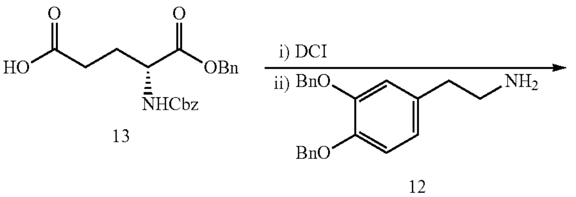

13

12 iii) $H_2$—Pd/C

-continued

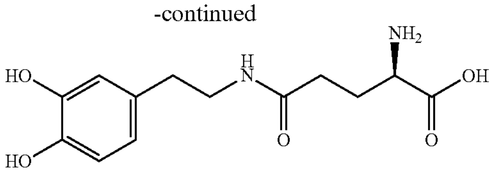

2

In a third example, compounds 3 and 4 may be prepared from chloromethyl carbamate 14, which itself may be prepared by reaction of dibenzyl dopamine 12 with chloromethyl chloroformate in the presence of a proton sponge. Coupling of chloromethyl carbamate 14 with either 11 or 13, followed by deprotection by hydrogenation in the presence of Pd/C gave the target compounds 3 and 4 as shown in, for example, Scheme 3, below.

SCHEME 3

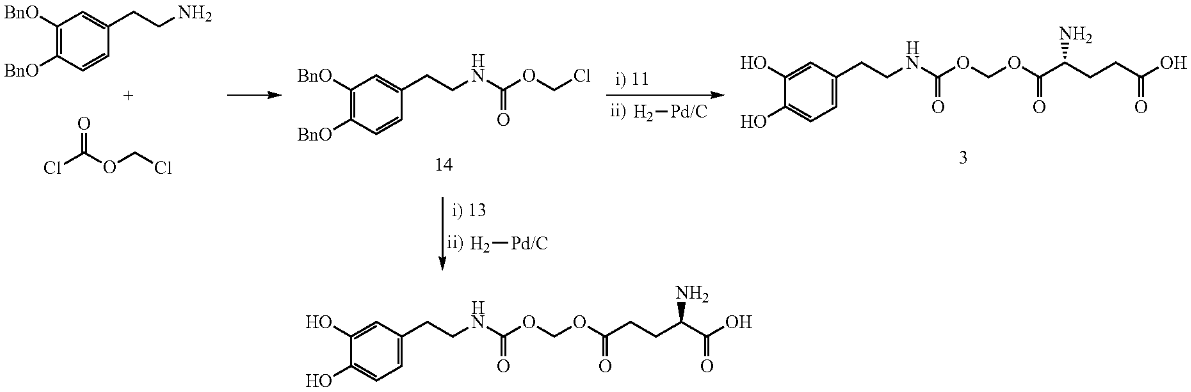

14

3

4

In a fourth example, compounds 5 and 6 may be prepared from the bis-Cbz-lysine derivative 15 using the route laid out in Scheme 1 for compound 1 or the route described in Scheme 3 for compound 3 as shown in, for example, Scheme 4, below.

SCHEME 4

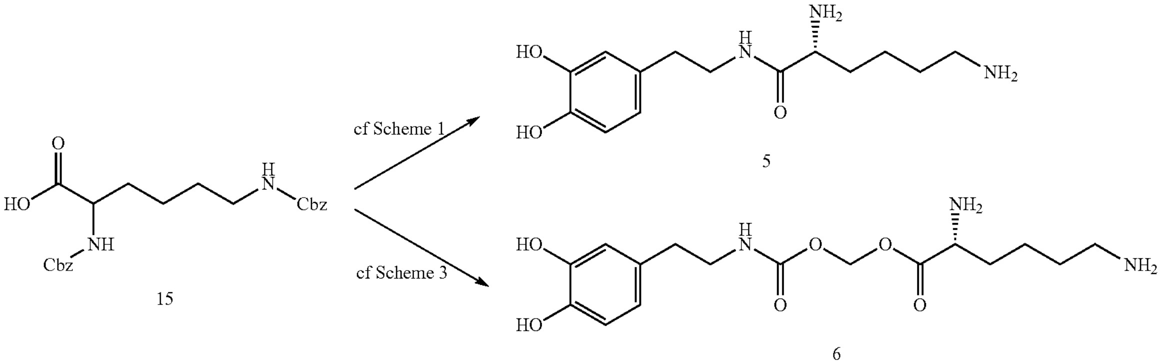

15

5

6

In a fifth example, the coupling of meglumine to dopamine may require selective protection of the secondary alcohols in meglumine. Initial protection of the primary alcohol with a TBDMS group followed by acylation of the four secondary alcohol functional groups and subsequent deprotection of the primary alcohol may give compound 16 as shown in, for example, Scheme 5, below. Coupling compound 16 with the chloromethyl carbamate 14 may proceed to intermediate 17, which may be deprotected to produce the target compound 7 as shown in, for example, Scheme 5, below.

SCHEME 5

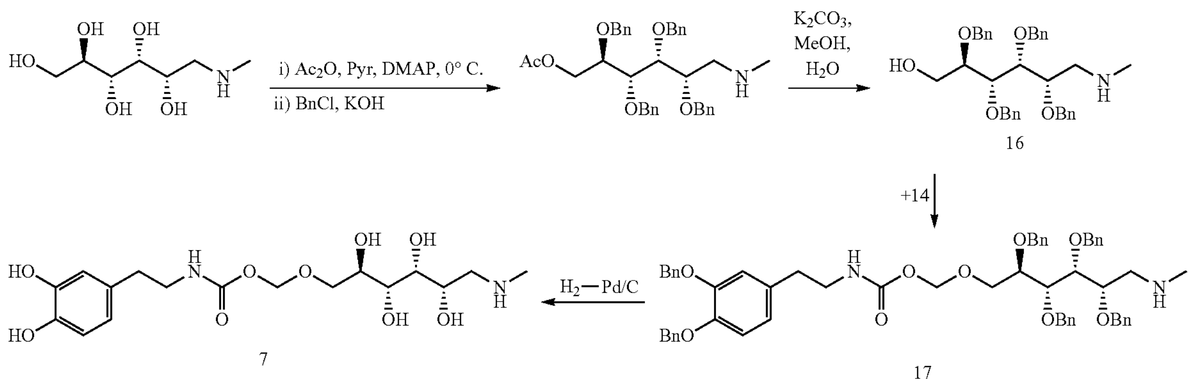

16

7

17

In a sixth example, coupling of hydroxyethyl piperazine ethane sulfonic acid may be succeeded by conversion to the disodium derivative with NaH in THF and treatment with the chloromethyl carbamate 14 at low temperature to avoid reaction with the sulphonate functional group a shown in, for example, Scheme 6, below.

-continued

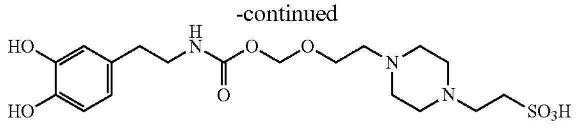

8

SCHEME 6

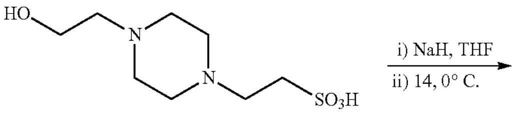

In a seventh example, compounds 9 and 10 may be prepared using similar methods as for compounds 5 and 6 as outlined and shown in Scheme 7, below.

SCHEME 7

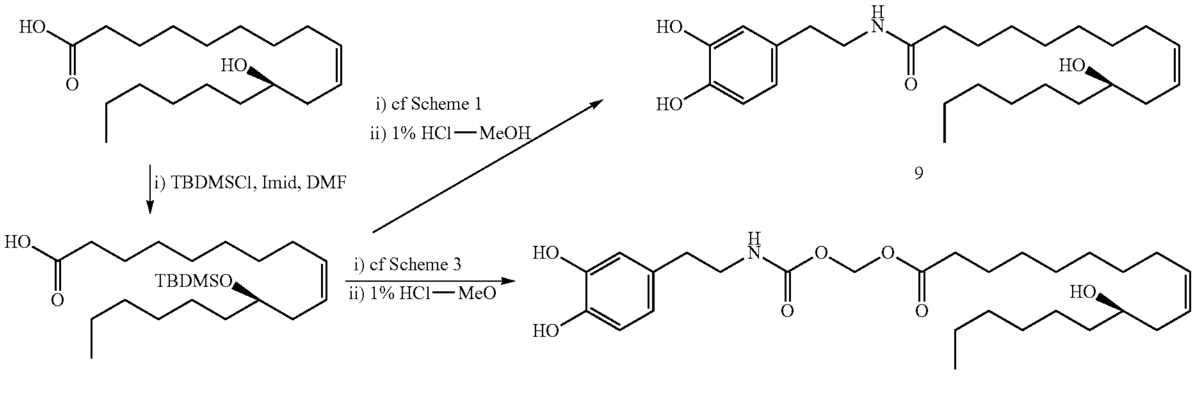

9

10

We claim:

1. A compound of Formula (D):

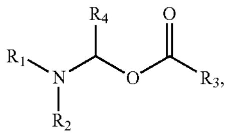

Formula D wherein, $R_1R_2N$ is selected from the group consisting of:

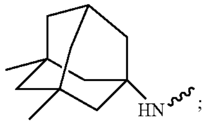

; and

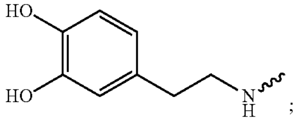

;

$R_4$ is H or $C_1$-$C_8$alkyl; and $R_3$ is selected from the group consisting of:

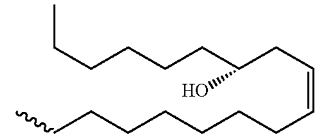

;

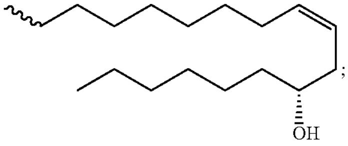

;

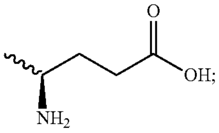

;

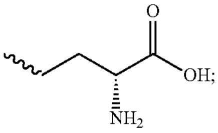

; and

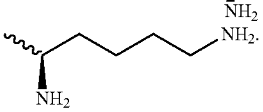

.

2. The compound of claim 1, wherein the compound is

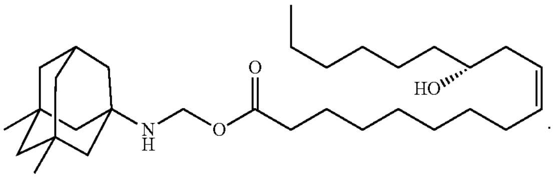 [SMILES: CCCCCC[C@@H](O)C/C=C\CCCCCCCC(=O)OCNC12CC3CC(C)(CC(C)(C3)C1)C2]

.

3. The compound of claim 1, wherein $R_1R_2N$ is

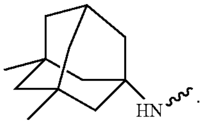

.

4. The compound of claim 1, wherein $R_1R_2N$ is

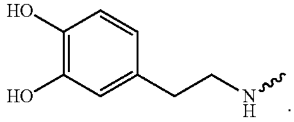

.

5. The compound of claim 1, wherein $R_3$ is

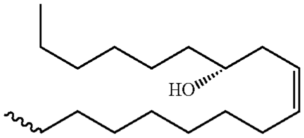

.

6. The compound of claim 1, wherein $R_3$ is

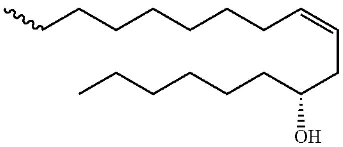

.

7. The compound of claim 1, wherein $R_3$ is

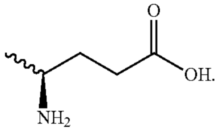

.

8. The compound of claim 1, wherein $R_3$ is

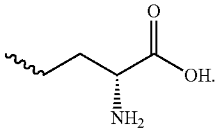

.

9. The compound of claim 1, wherein $R_3$ is

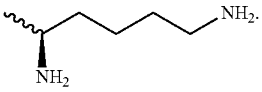

.

10. A pharmaceutical composition for intranasal administration comprising the compound of claim 1 and a pharmaceutically acceptable carrier.

* * * * *